(12) United States Patent
Dantus et al.

(10) Patent No.: US 9,048,632 B1
(45) Date of Patent: Jun. 2, 2015

(54) ULTRAFAST LASER APPARATUS

(71) Applicants: Marcos Dantus, Okemos, MI (US); Bai Nie, Lansing, MI (US)

(72) Inventors: Marcos Dantus, Okemos, MI (US); Bai Nie, Lansing, MI (US)

(73) Assignee: BOARD OF TRUSTEES OF MICHIGAN STATE UNIVERSITY, East Lansing, MI (US)

(*) Notice: Subject to any disclaimer, the term of this patent is extended or adjusted under 35 U.S.C. 154(b) by 147 days.

(21) Appl. No.: 13/833,529

(22) Filed: Mar. 15, 2013

(51) Int. Cl.
*H01S 3/23* (2006.01)
*H01S 3/16* (2006.01)
*A61B 18/00* (2006.01)
*A61B 1/00* (2006.01)

(52) U.S. Cl.
CPC ............. *H01S 3/2308* (2013.01); *H01S 3/1618* (2013.01); *A61B 2018/00577* (2013.01); *A61B 1/00009* (2013.01)

(58) Field of Classification Search
CPC .................................................. H01S 3/2308
See application file for complete search history.

(56) References Cited

U.S. PATENT DOCUMENTS

| | | | | |
|---|---|---|---|---|
| 4,136,929 | A * | 1/1979 | Suzaki | 385/30 |
| 4,720,160 | A * | 1/1988 | Hicks, Jr. | 385/31 |
| 4,772,854 | A | 9/1988 | Silberberg | |
| 4,856,860 | A | 8/1989 | Silberberg et al. | |
| 5,499,134 | A | 3/1996 | Galvanauskas et al. | |
| 6,421,171 | B1 * | 7/2002 | Bayart et al. | 359/341.1 |
| 6,979,798 | B2 | 12/2005 | Gu et al. | |
| 7,113,327 | B2 | 9/2006 | Gu et al. | |
| 7,142,789 | B1 | 11/2006 | Weiner et al. | |
| 7,330,301 | B2 * | 2/2008 | Harter | 359/333 |
| 7,439,497 | B2 | 10/2008 | Dantus et al. | |
| 7,450,618 | B2 | 11/2008 | Dantus et al. | |
| 7,486,436 | B1 * | 2/2009 | Kuksenkov et al. | 359/333 |
| 7,567,596 | B2 | 7/2009 | Dantus et al. | |
| 7,570,851 | B2 | 8/2009 | Weiner | |
| 7,583,710 | B2 | 9/2009 | Dantus et al. | |
| 7,609,731 | B2 | 10/2009 | Dantus et al. | |
| 7,782,912 | B2 * | 8/2010 | Harter et al. | 372/6 |
| 7,852,488 | B2 | 12/2010 | Devos et al. | |
| 7,973,936 | B2 | 7/2011 | Dantus | |
| 8,040,929 | B2 * | 10/2011 | Imeshev et al. | 372/21 |
| 8,077,749 | B2 | 12/2011 | Shah | |
| 8,158,493 | B2 | 4/2012 | Shah et al. | |
| 8,208,504 | B2 | 6/2012 | Dantus et al. | |
| 8,208,505 | B2 | 6/2012 | Dantus et al. | |
| 8,265,110 | B2 | 9/2012 | Dantus et al. | |

(Continued)

OTHER PUBLICATIONS

Brixner, T. et al.; "Abstract—Femtosecond quantum control," Advances in Atomic, Molecular, and Optical Physics, vol. 45, 46: 1-54, 2001, one page.

(Continued)

*Primary Examiner* — Ari M Diacou
(74) *Attorney, Agent, or Firm* — Harness, Dickey & Pierce, P.L.C.

(57) ABSTRACT

A laser apparatus includes a fiber oscillator. In another aspect, an Ytterbium (Yb) doped fiber is employed. Another aspect provides an unamplified laser pulse emitted from an Yb fiber oscillator having a repetition rate less than 5 MHz and a pulse energy greater than 100 nJ. In still an additional aspect, a flexible Yb fiber has a length greater than 1 m which is capable of being looped with an outside loop diameter less than 150 mm. Another aspect provides for a fiber oscillator with passive optical fiber lengths of at least 10 meters, and more preferably more than 100 meters while having repetition rates less than 4 MHz.

14 Claims, 6 Drawing Sheets

(56) References Cited

U.S. PATENT DOCUMENTS

| | | | |
|---|---|---|---|
| 8,279,903 B2 | 10/2012 | Shah et al. | |
| 8,300,669 B2 | 10/2012 | Dantus et al. | |
| 8,311,069 B2 | 11/2012 | Dantus et al. | |
| 8,338,746 B2 | 12/2012 | Sun et al. | |
| 8,424,617 B2 | 4/2013 | Faircloth et al. | |
| 8,461,481 B2 | 6/2013 | Frey | |
| 8,493,651 B1* | 7/2013 | Hu et al. | 359/341.1 |
| 8,494,323 B2* | 7/2013 | Hoekman et al. | 385/50 |
| 8,511,401 B2 | 8/2013 | Zediker et al. | |
| 8,523,926 B2 | 9/2013 | Neev | |
| 8,585,686 B2* | 11/2013 | Bergt et al. | 606/4 |
| 8,600,243 B2 | 12/2013 | Miao et al. | |
| 8,618,470 B2 | 12/2013 | Dantus et al. | |
| 8,630,322 B2 | 1/2014 | Dantus et al. | |
| 8,633,437 B2 | 1/2014 | Dantus et al. | |
| 8,644,356 B2 | 2/2014 | Shah et al. | |
| 8,675,699 B2 | 3/2014 | Dantus et al. | |
| 8,785,813 B2 | 7/2014 | Shah et al. | |
| 2002/0003440 A1* | 1/2002 | Qian et al. | 327/21 |
| 2004/0240037 A1* | 12/2004 | Harter | 359/333 |
| 2005/0107773 A1* | 5/2005 | Bergt et al. | 606/4 |
| 2005/0226287 A1* | 10/2005 | Shah et al. | 372/25 |
| 2005/0238070 A1* | 10/2005 | Imeshev et al. | 372/21 |
| 2007/0199927 A1* | 8/2007 | Gu et al. | 219/121.69 |
| 2008/0130099 A1* | 6/2008 | Harter | 359/341.1 |
| 2008/0309931 A1 | 12/2008 | Silberberg et al. | |
| 2009/0188901 A1 | 7/2009 | Dantus | |
| 2009/0207869 A1 | 8/2009 | Dantus et al. | |
| 2009/0285249 A1* | 11/2009 | Gu et al. | 372/18 |
| 2010/0123075 A1 | 5/2010 | Dantus et al. | |
| 2011/0211600 A1 | 9/2011 | Dantus et al. | |
| 2012/0076504 A1 | 3/2012 | Dantus et al. | |
| 2012/0147911 A1 | 6/2012 | Dantus et al. | |
| 2012/0195330 A1* | 8/2012 | Cho et al. | 372/6 |
| 2012/0196454 A1 | 8/2012 | Shah et al. | |
| 2014/0088574 A1* | 3/2014 | Bergt et al. | 606/4 |
| 2014/0321486 A1 | 10/2014 | Da Costa Ribeiro De Miranda et al. | |

OTHER PUBLICATIONS

Brixner, T. et al.; "Abstact—Photoselective adaptive femtosecond control in the liquid phase," Nature, 414 (6859), 57-60, Nov. 1, 2009, one page.

Brixner, T. et al.; "Feedback-controlled optimization of amplified femtoseond laser pulses," Applied Physics B 68, 1999, pp. 281-284.

Brixner, T. et al.; "Generation and characterization of polarization-shaped femtosecond laser pulses"; Applied Physics B74 (Suppl), 2002; pp. S133-S144.

Brixner, T. et al; "Liquid-phase adaptive femtosecond quantum control: Removing intristic intensity dependencies," Journal of Chemical Physics, vol. 118, No. 8, Feb. 22, 2003, pp. 3692-3701.

Brixner, T. et al.; "Problem complexity in femtosecond quantum control," Chemical Physics 267, 2001, pp. 241-246.

Cerqueira, Arismar et al., "Full Nonlinear Conversion of Broadband Frequency Combs generated by Four-Wave Mixing in Highly Nonlinear Fibers," Optical Society of America, 2009, 4 pages.

Chichkov, Nikolai B. et al; "0.5 µJ pulses from a giant-chirp ytterbium fiber oscillator," Optics Express, vol. 19, No. 4, Feb. 14, 2011, pp. 3647-3650.

Chong, Andy et al.; "All-normal-dispersion femtosecond fiber laser," Optics Express, vol. 14, No. 21, Oct. 16, 2006, pp. 10095-10100.

Coello, Yves et al.; "Interference without an interferometer: a different approach to measuring, compressing, and shaping ultrashort laser pulses," J. Opt. Soc. Am. B, vol. 25, No. 6, Jun. 2008, pp. A140-A150.

"Coherent® Silhouette, Ultrafast Pulse Shaper," Key Features brochure, Web, Jan. 29, 2008, http://www.coherent.com/Lasers/index.cfm?Fuseaction=show.print&ID=1485, four pages.

"Coherent® Silhouette, Ultrafast Pulse Shaping and Measurement," brochure, Coherent, Inc., 2007, two pages.

Comstock, Matthew. et al.; "Femtosecond Photon Echo Measurements of Electronic Coherence Relaxation Between the X(1Eg+) and B(3II0u+) states of I2 in the Presence of He, Ar, N2, O2, C3H8," J. Chem. Phys., vol. 119, No. 13, Oct. 1, 2003, pp. 6546-6553.

Comstock, Matthew et al.; "Multiphoton intrapulse interference 6; binary phase shaping," Optics Express Opt. Soc. America USA, vol. 12, No. 6, Mar. 22, 2004, pp. 1061-1066.

Comstock, Matthew et al.; "Rotational Wavepacket Revivals for Phase Modulation of Ultrafast Pulses," Chemical Physics Letters, 372, 2003, pp. 739-744.

Comstock, Matthew et al.; "Ultrafast Laser Induced Molecular Alignment and Deformation: Experimental Evidence From Neutral Molecules and From Fragment Ions," J. Phys. Chem. A, vol. 107, No. 40, 2003, pp. 8271-8281.

Comstock, Matthew et al.; "Ultrafast Transient-Grating Study of Molecules After High Intensity Excitation," in Ultrafast Phenomena XII, 2000, two pages.

Dantus, Marcos; "Ahmed Zewail, Nobel Laureate in Chemistry," European Photochemistry Association (EPA) Newsletter, No. 69, Jul. 2000, five pages.

Dantus, Marcos; "Coherent Nonlinear Spectroscopy: From Femtosecond Dynamics to Control," Annu. Rev. Phys. Chem., 52, 2001, pp. 639-679.

Dantus, Marcos et al.; "Experimental Coherent Laser Control of Physicochemical Processes," Chem. Rev. 2004, 104, pp. 1813-1859.

Dantus, Marcos et al.; "Femtosecond Laser Observations of Molecular Vibration and Rotation," Nature, vol. 343, Feb. 22, 1990, pp. 737-739.

Dantus, Marcos; "Femtosecond Laser Pulses: Principles and Experiments;" (Book Review) J. Am. Chem. Soc., vol. 121, No. 37, 1999, pp. 8677-8678.

Dantus, Marcos et al.; "Femtosecond Real-Time Probing of Reactions. II. The Dissociation Reaction of ICN," J. Chem. Phys., vol. 89, No. 10, Nov. 15, 1988, pp. 6128-6140.

Dantus, Marcos et al.; "Femtosecond Real-Time Probing of Reactions. V. The reaction of IHgI," J. Chem. Phys., vol. 91, No. 12, Dec. 15, 1989, pp. 7437-7450.

Dantus, Marcos; GeneticAlgorithm-v4.nb to simulate an adaptive genetic algorithm, Oct. 2001, pp. 1-7.

Dantus, Marcos; "Laser Control of Chemical Reactions," Chemical & Engineering News, vol. 79, 2001, p. 191.

Dantus, Marcos, et al.; "MIIPS characterizes and corrects femtosecond pulses," Ultrafast Optical Systems, Laser Focus World, May 2007, XP001539450, four pages.

Dantus, Marcos et al.; "Real-Time Femtosecond Probing of "Transition States" in Chemical Reactions," J. Chem. Phys., vol. 87, No. 4, Aug. 15, 1987, pp. 2395-2397.

Dantus, Marcos et al.; "Two-Photon Microscopy with Sub-8fs Laser Pulses," Frontiers in Optics/Laser Science XXVI, Oct. 24-28, 2010, 18 pages.

Dantus, Marcos; "Ultrafast Probing and Control of Molecular Dynamics: Beyond the Pump-Probe Method"; Kuhn & Weyh SRZ, Sep. 4, 2001, pp. 169-188.

Dantus, Marcos et al.; "Ultrafast Spectroscopy," Encyclopedia of Applied Physics, vol. 22, 1998, pp. 431-456.

"DCF-YB-10/128P Yb Doped Double Clad Fiber," specifications sheet, CorActive High-Tech Inc., believed to have been published in March of 2011, one page.

Dela Cruz, Johanna M. et al.; "Coherent Control Improves Biomedical Imaging With Ultrashort Shaped Pulses," Journal of Photochemistry and Photobiology A: Chemistry 180, Mar. 2006, pp. 307-313.

Dela Cruz, Johanna M. et al.; "Multiphoton Intrapulse Interference 3: Probing Microscopic Chemical Environments," J. Phys. Chem. A, 108, 2004 pp. 53-58.

Dela Cruz, Johanna M., et al., "Quantitative Mass Spectrometric Identification of Isomers Applying Coherent Laser Control," Journal of Physical Chemistry A ACS USA, vol. 109, No. 38, Sep. 29, 2005, pp. 8447-8450, XP002431289, ISSN: 1089-5639, figure 1.

Dela Cruz, Johanna M. et al., "Use of coherent control methods through scattering biological tissue to achieve functional imaging," PNAS, vol. 101, No. 49, Dec. 7, 2004, pp. 16996-17001.

Dela Cruz, Johanna M. et al.; "Multidimensional analysis with shaped femtosecond pulses: identification of conformational and geometric isomers and mixtures using mass spectrometry," American Chemical Society. Abstracts of paper. At the national meeting,

(56) References Cited

OTHER PUBLICATIONS

American Chemical Society, Washington, D.C., U.S., vol. 230, Aug. 28, 2005, p. U418, XP009082815, ISSN: 0065-7727, the whole document.

Delfyett, Peter J. et al.; "Joint Time-Frequency Measurements of Mode-Locked Semiconductor Diode Lasers and Dynamics Using Frequency-Resolved Optical Gating," IEEE Journal of Quantum Electronics, vol. 35, No. 4, Apr. 1999, pp. 487-500.

Dennis, Michael L. et al.; "Grating sensor array demodulation by use of a passively mode-locked fiber laser," Optics Letters, vol. 22, No. 17, Sep. 1, 1997, pp. 1362-1364.

Dudley, J. M. et al.; "Direct measurement of pulse distortion near the zero-dispersion wavelength in an optical fiber by frequency-resolved optical gating"; Optics Letters, vol. 22, No. 7, Apr. 1, 1997, pp. 457-459.

Fermann, M. E. et al., "Additive-pulse-compression mode locking of a neodymium fiber laser", Optics Letters, vol. 16, No. 4, Feb. 15, 1991, pp. 244-246.

Galvanauskas, Almantas et al.; "Hybrid diode-laser fiber-amplifier source of high-energy ultrashort pulses," Optics Letters, vol. 19, No. 14, Jul. 15, 1994, pp. 1043-1045.

Gunaratne, Tissa et al.; "Influence of Bandwidth and Phase Shaping on Laser Induced Breakdown Spectroscopy With Ultrashort Laser Pulses," Chemical Physics Letters 423, Apr. 3, 2006, pp. 197-201.

Gunn, Jess M. et al.; "Polarization and Phase Control of Remote Surface-Plasmon-Mediated Two-Photo-Induced Emission and Waveguiding" Nano Letters American Chem. Soc. USA, vol. 6, No. 12, Aug. 2006, pp. 2804-2809.

Haner, M. et al.; "Generation of programmable, picosecond-resolution shaped laser pulses by fiber-grating pulse compression," Optics Letters, vol. 12, No. 6, Jun. 1987, pp. 398-400.

Horowitz, Moshe et al.; "Control of Noiselike Pulse Generation in Erbium-Doped Fiber Lasers," IEEE Photonics Technology Letters, vol. 10, No. 10, Oct. 1998, pp. 1389-1391.

Horowitz, M. et al.; "Noiselike pulses with a broadband spectrum generated from an erbium-doped fiber laser," Optics Letters, vol. 22, No. 11, Jun. 1 1997, pp. 799-801.

Huang, Huan et al.; "Femtosecond fiber-laser-based laser-induced breakdown spectroscopy," SPIE Paper No. 8358-43, SPIE Defense, Security and Sensing, Apr. 23-27, 2012, nine pages.

Kalashnikov, V. L. et al.; "Chirped-pulse oscillators: A unified standpoint," Physical Review A 70, 043829, 2009, pp. 043829-1-043829-10.

Kang, Jin U.; "Broadband quasi-stationary pulses in mode-locked fiber ring laser," Optics Communications, 182, Aug. 15, 2000, pp. 433-436.

Khan, MD Saad et al.; "Broadband Supercontinuum Generation with Excellent Spectral Stability from a Highly-Nonlinear Fibre using an Amplified Noiselike-Pulse Train," ECOC 2005 Proceedings, vol. 1, Paper Mo3.5.5, pp. 61-62.

Konorov, S. O. et al., "Laser Breakdown with Millijoule Trains of Picosecond Pulses Transmitted through a Hollow-Core Photonic-Crystal Fiber," Laser Physics, vol. 13, No. 4, 2003, pp. 652-656.

Krampert, Gerhard; "Femtosecond Quantum Control and Adaptive Polarization Pulse Shaping", Dissertation zur Erlangung des naturwissenschaftlichen Doktorgrades der Bayerischen Julius-Maximilians-Universitat Wurzburg, Sep. 9, 2004, 135 pages.

Limpert, J.; "All fiber chirped-pulse amplification system based on compression in air-guiding photonic bandgap fiber," Optics Express, vol. 11, No. 24, Dec. 1, 2003, pp. 3332-3337.

Lozovoy, Vadim V. et al.; "Cascaded Free-Induction Decay Four-Wave Mixing," Chemical Physics 266, 2001, pp. 205-212.

Lozovoy, Vadim V. et al.; "Femtosecond Spectrally Dispersed Three-Pulse Four-Wave Mixing: The Role of Sequence and Chirp in Controlling Intramolecular Dynamics;" Journal of Raman Spectroscopy 31, 2000, pp. 41-49.

Lozovoy, Vadim V. et al.; "Multiphoton intrapulse interference. II. Control of two- and three-photon laser induced fluorescence with shaped pulses," Journal of Chemical Physics, vol. 118, No. 7; Feb. 15, 2003, pp. 3187-3196.

Lozovoy, Vadim V. et al.: "Multiphoton Intrapulse Interference. IV. Ultrashort Laser Pulse Spectral Phase Characterization and Compensation;" Optics Letters, vol. 29, No. 7, Apr. 1, 2004; pp. 775-777.

Lozovoy, Vadim V. et al.; "Photon Echo Pulse Sequences With Femtosecond Shaped Laser Pulses as a Vehicle for Molecule-Based Quantum Computation," Chemical Physics Letters 351, Jan. 10, 2002, pp. 213-221.

Lozovoy, Vadim V. et al.; "Spectral Phase Optimization of Femtosecond Laser Pulses for Narrow-Band, Low-Background Nonlinear Spectroscopy," Optics Express, vol. 13, No. 26, Dec. 26, 2005, pp. 10882-10887.

Lozovoy, Vadim V. et al.; "Systematic Control of Nonlinear Optical Processes Using Optimally Shaped Femtosecond Pulses," ChemPhysChem, Wiley-VCH Verlag GmbH & Co. KGaA, Weinheim, 6, 2005, pp. 1970-2000.

Lozovoy, Vadim V. et al.; "The Role of Microscopic and Macroscopic Coherence in Laser Control," Chemical Physics 267, 2001, pp. 99-114.

Lozovoy, Vadim V. et al.; "The Role of Pulse Sequences in Controlling Ultrafast Intramolecular Dynamics With Four-Wave Mixing," Int. Rev. In Physical Chemistry, vol. 19, No. 4, 2000, pp. 531-552.

Lozovoy, Vadim V. et al; "What Role Can Four-Wave Mixing Techniques Play in Coherent Control?" Advances in Multiphoton Processes and Spectroscopy 14, and Quantum Control of Molecular Reaction Dynamics, edited by R.J. Gordon and Y. Fujimura, World Scientific, Singapore, 2000, pp. 62-79.

Mukhopadhyay, Pranab K. et al.; "All-Fiber Low-Noise High-Power Femtosecond Yb-Fiber Amplifier System Seeded by an All-Normal Dispersion Fiber Oscillator," IEEE Journal of Selected Topics in Quantum Electronics, vol. 15, No. 1, Jan./Feb. 2009, pp. 145-152.

Nie, Bai et al.; "An Ultrafast Fiber Laser with Self-Similar Evolution in the Gain Segment," Ultrafast Optics, Dec. 2011, p. 47.

Nie, Bai et al.; "Multimodal microscopy with sub-30 fs Yb fiber laser oscillator," Biomedical Optics Express, vol. 3, No. 7, Jul. 1, 2012, pp. 1750-1756.

Ortac, B. et al.; "200 nJ pulse energy femtosecond Yb-doped dispersion compensation free fiber oscillator," SPIE, vol. 6873, 2008, pp. 68730R-1-68730R-7.

Pastirk, Igor et al.; "2D (time-frequency) Femtosecond Four-Wave Mixing at $10^{14}$ W/cm$^2$: Molecular and Electronic Response;" Symposium on Optical Pulse and Beam Propagation III, Photonics West, 2001, pp. 1-3.

Pastirk, Igor et al.; "Control and Characterization of Intramolecular Dynamics with Chirped Femtosecond Three-Pulse Four-Wave Mixing," J. Phys. Chem. A, vol. 103, No. 49, Sep. 23, 1999, pp. 10226-10236.

Pastirk, Igor et al.; "Femtosecond Ground State Dynamics of Gas Phase N2O4 and NO2," Chemical Physics letters, vol. 349, Nov. 23, 2001, pp. 71-78.

Pastirk, Igor et al.; "Femtosecond Photo Echo and Virtual Echo Measurements of the Vibronic and Vibrational Coherence Relaxation Times of Iodine Vapo," Chemical Physics Letters, vol. 333, Jan. 5, 2001, pp. 76-82.

Pastirk, Igor, et al., "Multidimensional Analytical Method Based on Binary Phase Shaping of Femtosecond Pulses," Journal of Physical Chemistry A Letters, vol. 109, No. 11, Feb. 23, 2005, pp. 2413-2416.

Pastirk, I. et al., "No loss spectral phase correction and arbitrary phase shaping of regeneratively amplified femtosecond pulses using MIIPS," Optics Express, vol. 14, No. 20, Oct. 2, 2006, pp. 9537-9543.

Pastrik, Igor. et al; "Quantum Control of the Yield of a Chemical Reaction," Journal of Chemical Physics, vol. 108, No. 11, Mar. 15, 1998, pp. 4375-4378.

Pastirk, Igor et al; "Selective two-photon microscopy with shaped femtosecond pulses," Optics Express vol. 11, No. 14, 2003, pp. 1695-1701.

Pastrik, Igor et al.; "Sequences for Controlling Laser Excitation with Femtosecond Three-Pulse Four-Wave Mixing," The Royal Society of Chemistry, vol. 113, 1999, pp. 401-424.

Rhy, HeeYeal et al.; "Noiselike pulse generation in a fiber laser by use of nonlinear differential filtering with a nonlinear birefringent loop mirror," Department of Physics, Korea Advanced Institute of Science and Technology, IEEE, 1999, pp. 1135-1136.

(56) References Cited

OTHER PUBLICATIONS

Richardson, D. J. et al.; "320 fs Generation With Passively Mode-Locked Erbium Fibre Laser," Electronics Letters, vol. 27, No. 9, Apr. 25, 1991, pp. 730-732.

Sato, Masamichi, et al.; "Adaptive Pulse Shaping of Femtosecond Laser Pulses in Amplitude and Phase Through a Single-Mode Fiber by Referring to Frequency-Resolved Optical Gating Patterns", Jpn. J. Appl. Phys., vol. 41, Part 1 No. 6A, Jun. 2002, XP002436366, pp. 3704-3709.

Scaffidi, Jon et al.; "Spatial and Temporal Dependence of Interspark Interactions in Femtosecond-Nanosecond Dual Pulse Laser-Induced Breakdown Spectroscopy", Applied Optics, vol. 43, No. 27, Sep. 20, 2004, XP-002462408, pp. 5243-5250.

Seong, N. H. et al.; "A New Figure-Eight Fiber Laser Based on a Dispersion-Imbalanced Nonlinear Optical Loop Mirror With Lumped Dispersive Elements," IEEE Photonics Technology Letters, vol. 14, No. 4, Apr. 2002, pp. 459-461.

Silberberg, Yaron; "Physics at the attosecond frontier," Nature, vol. 414, Nov. 29, 2001, pp. 494-495.

Tada, Junji et al.; "Adaptively controlled supercontinuum pulse from a microstructure fiber for two-photon excited fluorescence microscopy," Applied Optics, vol. 46, No. 15, May 20, 2007, pp. 3023-3030.

Takushima, Y. et al; "87 nm bandwidth noise-like pulse generation from erbium-dopes fibre laser," Electronics Letters, vol. 41, No. 7, Mar. 31, 2005, two pages.

Tamaki, Y. et al.; "Phase-matched third-harmonic generation by nonlinear phase shift in a hollow fiber," Lasers and Optics Applied Physics B, vol. 67, 1998, pp. 59-63.

Tang, D. Y. et al.; "Soliton collapse and bunched noise-like pulse generation in a passively mode-locked fiber ring laser," Optics Express, vol. 13, No. 7, Apr. 4, 2005, pp. 2289-2294.

Trebino, R. et al; "Measuring Ultrashort Laser Pulses Just Got a Lot Easier!" Optics & Photonics News, Jun. 2001, pp. 22-25.

Trebino, Rick et al.; "Measuring ultrashort laser pulses in the time-frequency domain using frequency-resolved optical gating," Rev. Sci. Instrum. vol. 68, No. 9, Sep. 1997, pp. 3277-3295.

Trebino, Rick et al.; "The Dilemma of Ultrashort-Laser-Pulse Intensity and Phase Measurement and Applications," IEEE Journal of Quantum Electronics, vol. 35, No. 4, Apr. 1999, pp. 418-420.

Trebino, Rick, et al., "Using phase retrieval to measure the intensity and phase of ultrashort pulses: frequency-resolved optical gating," J. Opt. Soc. Am. A, vol. 10, No. 5, May 1993, pp. 1101-1111.

Weiner, A. M. et al.; "Encoding and decoding of femtosecond pulses", Optics Letters, vol. 13, No. 4, Apr. 1988, pp. 300-302.

Weiner, A. M.; "Enhancement of coherent charge oscillations in coupled quantum wells by femtosecond pulse shaping," J. Opt. Soc. Am. B, vol. 11, No. 12, Dec. 1994, pp. 2480-2491.

Weiner, A. M., et al., "Femtosecond multiple-pulse impulsive stimulated Raman scattering spectroscopy," J. Opt. Soc. Am. B., vol. 8, No. 6, Jun. 1991, pp. 1264-1275.

Weiner, A. M.; "Femtosecond Optical Pulse Shaping and Processing," Prog. Quant. Electr., vol. 19, 1995, pp. 161; 230-233.

Weiner, Andrew M. et al.; "Femtosecond Pulse Shaping for Synthesis, Processing and Time-to-Space Conversion of Ultrafast Optical Waveforms," IEEE Journal of Selected Topics in Quantum Electronics, vol. 4, No. 2, Mar./Apr. 1998, pp. 317-331.

Weiner, A. M., "Femtosecond pulse shaping using spatial light modulators," Review Article, Review of Scientific Instruments, vol. 71, No. 5, May 2000, pp. 1929-1960.

Weiner, A. M. et al. "Generation of terahertz-rate trains of femtosecond pulses by phase-only filtering," Optics Letters, vol. 15, No. 1, Jan. 1, 1990, pp. 51-53.

Weiner, A. M. et al.; "High-resolution femtosecond pulse shaping," J. Opt. Soc. Am. B., vol. 5, No. 8, Aug. 1988, pp. 1563-1572.

Weiner, A. M. et al.; "Programmable femtosecond pulse shaping by use of a multielement liquid-crystal phase modulator," Optics Letters, vol. 15, No. 6, Mar. 15, 1990, pp. 326-328.

Weiner, Andrew M. et al.; "Programmable Shaping of Femtosecond Optical Pulses by Use of 128-Element Liquid Crystal Phase Modulator," IEEE Journal of Quantum Electronics vol. 28, No. 4, Apr. 1992, pp. 908-920.

Weiner, A. M. et al.; "Shaping of femtosecond pulses using phase-only filters designed by simulated annealing," Journal of the Optical Society of America A USA, vol. 10, No. 5, May 1993, pp. 1112-1120.

Weiner, A. M. et al.; "Spectral holography of shaped femtosecond pulses," Optics Letters, vol. 17, No. 3, Feb. 1, 1992, pp. 224-226.

Xu, Bingwei et al.; "Pulse shaping of octave spanning femtosecond laser pulses," Optics Express, vol. 14, No. 22, Oct. 30, 2006, pp. 10939-10944.

Xu, Bingwei et al.; "Quantitative investigation of the multiphoton intrapuse interference phase scan method for simultaneous phase measurement and compensation of femtosecond laser pulses," J. Opt. Soc. Am. B, vol. 23, No. 4, Apr. 2006, pp. 750-759.

Xu L. et al.; "Experimental generation of an ultra-broad spectrum based on induced-phase modulation in a single-mode glass fiber," Optics Communications, 162, Apr. 15, 1999, pp. 256-260.

Xu, J. H., et al., "Study of Pulse Compression from 1.5 µm Distributed Feedback Lasers by a Gires-Tournois Interferometer," Fiber and Integrated Optics, vol. 13, 1994, pp. 365-372.

\* cited by examiner

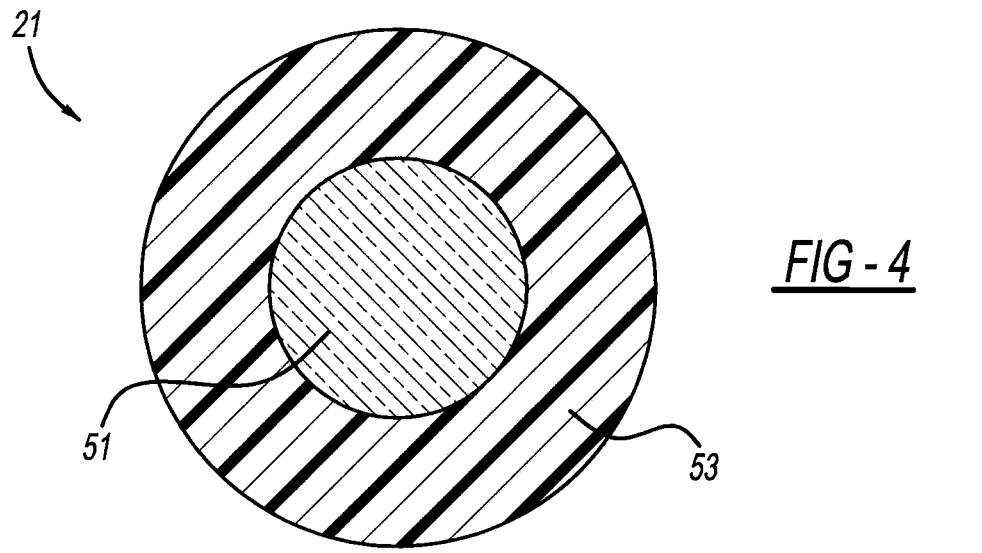
FIG - 4
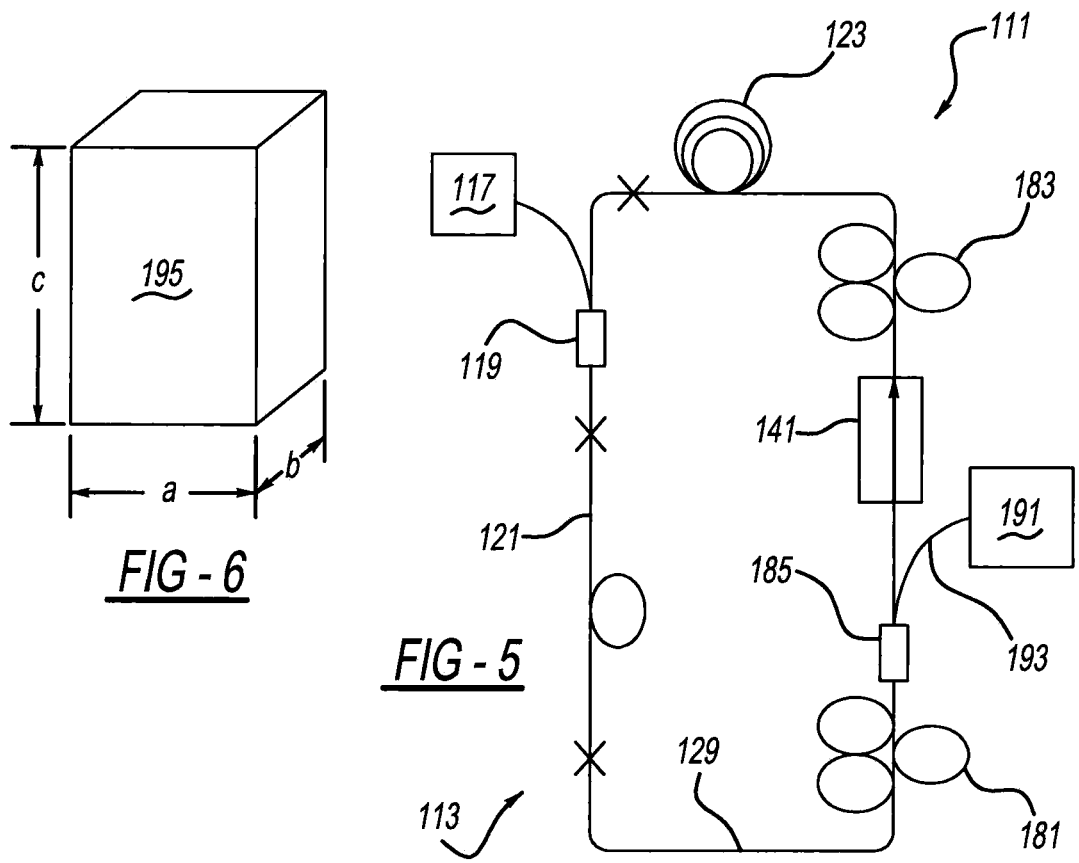
FIG - 6
FIG - 5

ULTRAFAST LASER APPARATUS

STATEMENT OF GOVERNMENT INTEREST

This invention is made with government support under Grant No. NSF 1014538 awarded by the United States National Science Foundation. The government has certain rights in the invention.

BACKGROUND AND SUMMARY

The present invention generally relates to lasers and more particularly to a laser apparatus including a fiber oscillator.

An ultrafast fiber amplifier is disclosed in U.S. Pat. No. 7,113,327 entitled "High Power Fiber Chirped Pulse Amplification System Utilizing Telecom-Type Components," which issued to Gu et al. on Sep. 26, 2006, and is incorporated by reference herein. This system follows a traditional approach towards generating high pulse energies from fiber lasers. The guidelines being outlined in the publication of A. Galvanauskas and M. Fermann, "Hybrid Diode-Laser Fiber-Amplifier Source of High-Energy Ultrashort Pulses," *Optics Letters*, Vol. 19, No. 14, 1043 (1994), state that high peak intensities inevitably lead to strong nonlinear effects and pulse breakup. The publication further states that the only way to avoid this problem is to maintain sufficiently low peak powers in the amplifier through the use of stretched or chirped pulses. Fiber laser design has not deviated from those guidelines, avoiding nonlinear optical effects and pulse break up through the introduction of pulse stretching optics before power amplification stages. While staying within these guidelines, which require complexity in the form of multiple amplification stages, commercial amplified fiber laser sources now reach tens and even hundreds of micro-Joules per pulse. These sources therefore use multiple stages of amplification to separate the gain into stages to make it more manageable, chirped pulse amplification stretching the pulse by five to six orders of magnitude, and the use of large mode area fiber in order to minimize the peak intensity within the fiber. Minimizing peak intensity is used in order to minimize nonlinear optical processes which have been considered detrimental by causing self-phase modulation, intensity induced dispersion, and pulse break up.

The publication M. Horowitz et al., "Noiselike Pulses with a Broadband Spectrum Generated from an Erbium-Doped Fiber Laser," *Optics Letters* 22, 799 (Jun. 1, 1997) teaches away from erbium-doped fiber lasers. The first page of this publication states that "the power of such sources is limited" and "a pulsed erbium-doped fiber laser . . . generates a train of high-intensity, broadband, noiselike pulses." Generally, optical "noise" is undesirable and to be avoided. The goal of Horowitz is to produce a short coherence length light source and not an efficient laser source. Furthermore, Horowitz comments in the last column: "Our laser cannot support short pulses because of the strong positive dispersion and the significant birefringence, which introduces significant PDD" (polarization-dependent delay).

The first page of the publication B. Ortac et al., "200 nJ Pulse Energy Femtosecond Yb-Doped Dispersion Compensation Free Fiber Oscillator," *Proc. of SPIE*, Vol. 6873 (2008) teaches the difficulties with power scaling mode-locked fiber lasers "[m]ainly, due to the tight confinement of the light over considerably long lengths nonlinear effects, mainly Kerr-nonlinearity, avoid self-consistent pulse evolution inside a fiber laser resonator and hinder the pursuit of higher pulse energies from mode-locked fiber lasers. Besides the necessary balance between dispersion and nonlinearity, which can be supported by spectral filtering, the overdriving of the effective saturable absorber can arise as a further energy scaling restriction." This conventional oscillator uses a 51 cm long large-mode-area fiber with an outer width of 1.4 mm, which is essentially inflexible.

The publication of V. L. Kalashnikov and A. Apolonski, "Chirped-Pulse Oscillators: A Unified Standpoint," *Physical Review A*, Vol. 79, 043821 (2009), second column, describes the theory of high-power oscillators and indicates that "energy scaling requires a large negative" net-group-delay-dispersion, "the soliton obtained has a large width, and . . . it is not compressible linearly" because "the peak power $P_0$ has to be kept lower than the threshold value $P_{th}$ in order to avoid soliton destabilization." Thus, "one can estimate the maximum attainable energy as $E=2P_{th}T$," where T is the soliton width. What Kalashnikov and Apolonski have failed to recognize, is that high intensity pulse trains that are desirable for a number of commercial applications can be obtained from lasers that do not avoid soliton destabilization. In other words, this publication followed the conventional literature in fiber laser design and teaches away from exploring regimes outside single soliton stability. The use of an all-normal-dispersion femtosecond fiber laser design, introduced by A. Chong et al., "All-Normal-Dispersion Femtosecond Fiber Laser," *Optics Express*, Vol. 14, No. 21, 10095 (2006), discusses the need to keep intracavity dispersion in the range of 0.04 to 0.10 $ps^2$ in order to obtain femtosecond pulses from a fiber oscillator.

In accordance with the present invention, a laser apparatus includes a fiber oscillator. In another aspect, an Ytterbium (Yb) doped fiber is employed. Another aspect provides an unamplified laser pulse emitted from an Yb fiber oscillator having a repetition rate less than 10 MHz and a pulse energy greater than 100 nJ. In still an additional aspect, the entire laser includes a flexible fiber, with at least one section greater than 10 m, and more preferably greater than 100 m, which is capable of being looped with an outside loop diameter less than 150 mm, and more preferably less than 125 mm. Another aspect provides for a fiber oscillator with passive optical fiber lengths of at least 10 m, and more preferably more than 100 m while having repetition rates less than 10 MHz. A further aspect employs an oscillator design that contains extremely high positive dispersion (greater than 1 $ps^2$), and/or an oscillator that exceeds the threshold of soliton stability by design. Yet a different aspect uses a fiber oscillator to produce discrete femtosecond sub-pulses clustered together in a time period less than 200 fs, without amplification and/or pulse shaping. A method of using an ultrafast laser apparatus is also provided.

The laser apparatus of the present invention is advantageous over traditional devices. For example, greater laser pulse energy can be emitted with lower repetition rates, in compact portable units, and at significantly lower costs than multi-stage amplified systems. The flexible nature of the flexible gain and passive fibers used allows for a very long fiber to be tightly wound, yet providing a high energy pulse output without an additional expensive and heavy amplifier, thereby fitting within the portable unit. The tightly wound fiber is also advantageous, when compared to relatively inflexible large-mode-area fibers by not exhibiting optical degradation or distortion and resulting in a more compact unit. The slowness and low repetition rate concerns with traditional Q-switches are also avoided since no Q-switch is needed or desired with the present laser apparatus. The present laser apparatus additionally has discrete sub-pulses clustered together within a very short time period, with each sub-pulse having an ultrafast (such as less than 100 femtosecond) duration, yet the clustered sub-pulses are insensitive to dispersion while increasing the energy delivered by the laser to the target without the need for amplification. An oscillator that results in high energy 0.1-1 uJ ultrafast pulses at 0.5-10 MHz is ideally suited for material processing, ablation and spectroscopy. Such ablation includes dental cornea and cataract surgery. Furthermore, the present laser apparatus is ideally suited for Laser-Induced Breakdown Spectroscopy ("LIBS"), selected Raman excitation, and endoscopy. Additional advantages and features of the present laser apparatus and method will become apparent from the following description and claims, as well as the appended drawings.

BRIEF DESCRIPTION OF THE DRAWINGS

FIG. 4 is a cross-sectional view through an oscillator fiber of the ultrafast laser apparatus;

FIG. 5 is a diagrammatic view showing a production, portable embodiment of the ultrafast laser apparatus;

FIG. 6 is a diagrammatic perspective view showing a housing unit of the portable ultrafast laser apparatus;

DETAILED DESCRIPTION

Figure 1:
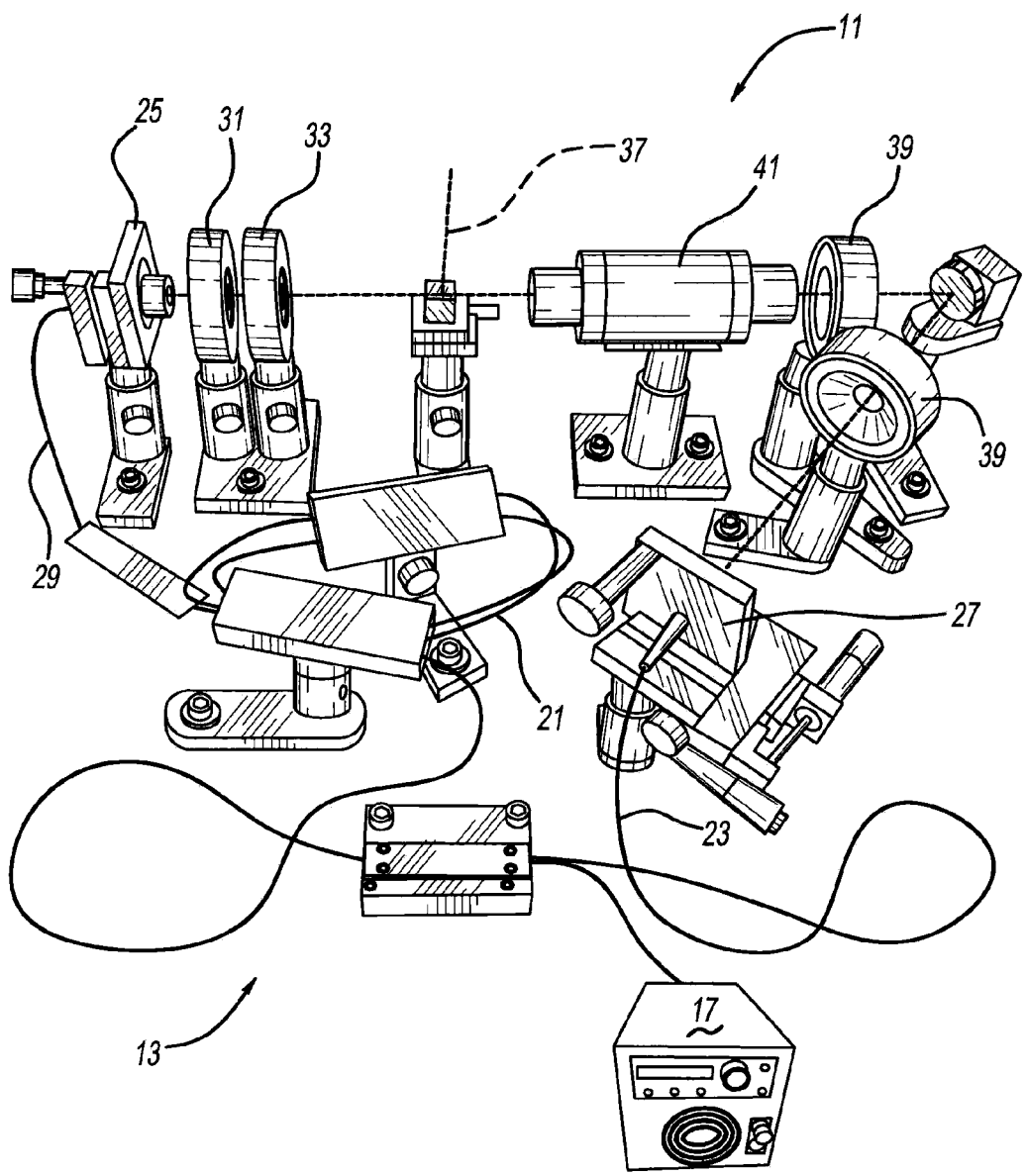
FIG. 1 is a perspective view showing a laboratory setup of the ultrafast laser apparatus.
Figure 2:
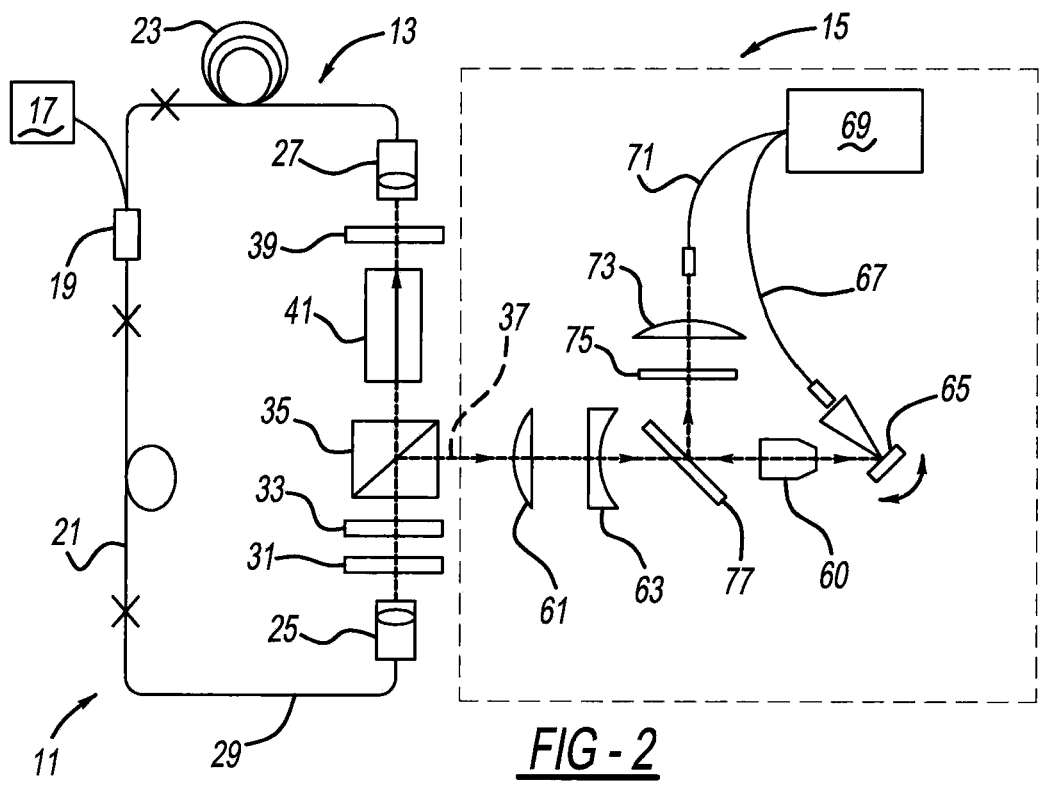
FIG. 2 is a diagrammatic view showing the laboratory setup of the ultrafast laser apparatus.

An ultrafast laser apparatus 11 is shown in FIGS. 1 and 2. Apparatus 11 includes a fiber laser oscillator 13 used with a Laser-Induced Breakdown Spectroscopy ("LIBS") system 15. A laboratory setup of this LIBS apparatus is illustrated wherein a laser beam pulse or output is focused to form a plasma plume which atomizes a sample or specimen through surface ablation. Atomic emission lines of the specimen are then detected.

A 976 nm diode pump laser 17 emits an initial laser beam through a fiber combiner 19. An Yb doped single-mode gain fiber 21 and a passive fiber 23 are connected on either side of fiber combiner 19. Collimator 25 is connected to gain fiber 21 via a 0.35 m passive, single-mode fiber 29. A half-wave plate 31, quarter wave plate 33 and polarized beam splitter 35 are placed between collimator 25 and a laser pulse output 37. On the other side, another half wave plate 39 and an isolator 41 are located between a collimator 27 and polarized beam splitter 35. The collimated laser beam enters passive, single-mode fiber 23 and connects with the fiber combiner 19.

Passive fiber 23 is at least 10 m long, more preferably at least 100 m or even 300 m long. Yb doped gain fiber 21 is at least 1 m long. However, optical fibers 21, 23 and 29 are advantageously flexible to allow them to be coiled or looped multiple times with an outside diameter of less than 125 mm, without optical degradation. Referring to FIG. 4, gain fiber 21 and passive fiber 23 and 29 have a glass core 51 and an outer concentric sheath 53 which are flexible enough to compactly coil the very long fiber 23. A suitable Yb doped, double clad gain fiber is model DCF-YB-10/128P from CorActive High-Tech, Inc. of Quebec City, Canada. This fiber advantageously allows for high pump absorption and high photodarkening resistance at high power. The present design is greater than the threshold peak intensity for soliton stability and uses much greater than 0.1 ps$^2$ positive group velocity dispersion, greater than 1 and even up to 4 ps$^2$.

One or both single mode fibers 23 and 29 have a length of approximately 100 m or even 200 m or greater, and are flexibly coiled. Single mode fibers 23 and 29 are passive such that they guide the light from gain fiber 21. It is noteworthy that this combination of very long fibers greatly reduces the cavity repetition rate to 2 MHz (for 100 m) or 1 MHz (for 200 m), which is advantageously an order of magnitude lower repetition rate than traditional fiber laser oscillator systems.

Figure 3A:
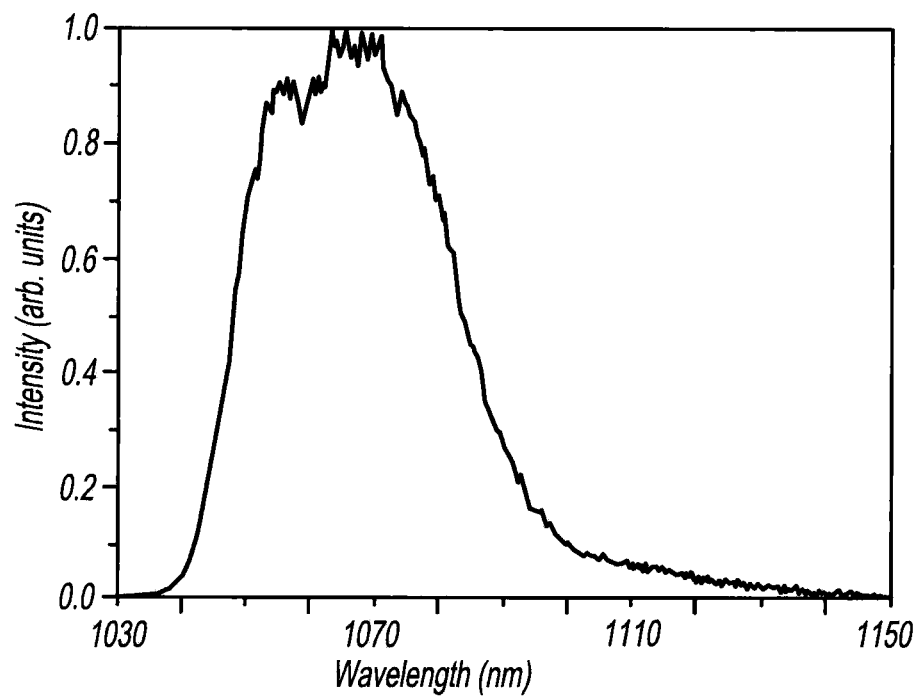
FIG. 3A is an expected output spectrum of the ultrafast laser apparatus.
Figure 3B:
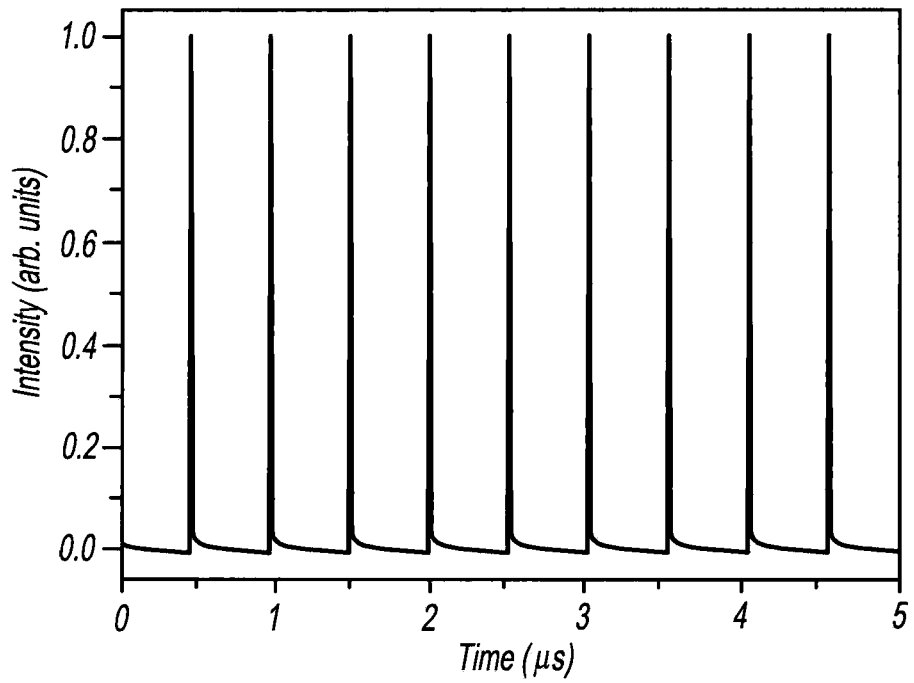
FIG. 3B is an expected output pulse train from the ultrafast laser apparatus.
Figure 3C:
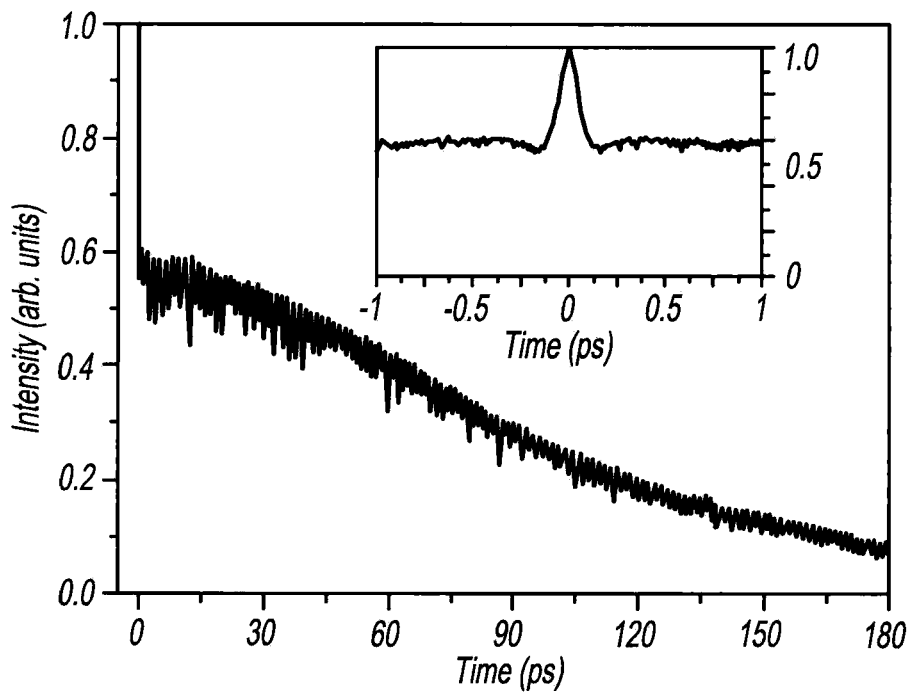
FIG. 3C is non-collinear AC trace for the ultrafast laser apparatus.

The expected oscillator performance is shown in FIGS. 3A-3C. FIG. 3A illustrates an expected output spectrum with average power of 640 mW at a repetition rate of 2 MHz. FIG. 3B illustrates an expected pulse train of laser output on the span of 5 µs. Moreover, an expected a non-collinear AC trace from 0 ps to +180 ps is shown in FIG. 3C, with the insert illustrating the same expected AC trace on a small range from −1 ps to +1 ps.

By adjusting the waveplates and pump power, different mode-locking states can be achieved due to the NPE mechanism. As viewed in FIG. 3C, with a 100 m long single mode fiber 29, the repetition rate is 2 MHz and the highest output power (640 mW) of stable mode-locking is achieved at 4.5 W pump power, resulting in 320 nJ of pulse energy. Lengthening fiber 29 to 200 m should cause the repetition rate to be reduced to 1 MHz and should cause the highest pump power for stable mode-locking to be 3 W. The corresponding output pulses have average power of 450 mW and 450 nJ pulse energy. In both cases, 1 MHz and 2 MHz, the pulse bursts occur as "single pulses," a behavior that is very different than when the laser is pumped with higher power and multi-pulsing occurs preventing the definition of a repetition rate. The expected averaged laser spectrum is broad and smooth as shown in FIG. 3A. As seen in FIG. 3C, the 2 MHz pulse train should be stable with peak-to-peak fluctuations on the order of ~1%. The mode-locking regime is robust and is also self-starting.

For output pulses with 640 mW average power at 2 MHz, an expected non-collinear AC result is shown in FIG. 3B (only half being shown). The averaged AC trace has a FWHM ~100 fs pulse in the center and a broad picosecond pedestal. The base line drops to below 0.1 at 180 ps. Not considering the center pulse, the FWHM of the AC trace is expected to be around 170 ps, corresponding to ~121 ps FWHM pulse duration.

The formation of these pulse trains is due to peak-power clamping in normal dispersion cavities using nonlinear polarization ("NPE") mode-locking. Each output pulse should contain a large number of <100 femtosecond sub-pulses with specific amplitude, phase and pulse duration. The number of sub-pulses and their time-delay determines the overall time duration of the pulse train. Each pulse train is slightly different, leading to the observed smooth average spectrum and broad AC pedestal.

Given that each pulse consists of a train of sub-pulses, the phase dependence of the output pulses is different than that of conventional femtosecond lasers. It is believed that the integrated SHG signal can increase about five times by applying negative second order dispersion (~−60,000 fs2) to the output pulses using a pulse shaper. The ratio between the peak of the spike at the center of the AC and the pedestal within a picosecond can be increased by two to three times. However, compared to normal femtosecond pulses, the sensitivity of this pulse train to dispersion is more than three orders of magnitude smaller than a comparable single-pulse laser. This implies that these pulses can be delivered by an optical fiber with minimal pulse broadening. The high energy of the <100 femtosecond pulse train makes this laser ideal for material processing such as in a micromachining unit 191 or LIBS unit 15 (with some different internal components).

As shown in FIG. 2, the output beam of the cavity is collimated with telescope lenses 61 and 63 before being directed to the LIBS detection unit 15, without compression. A 20x objective 60 (NA=0.4) is used to focus the pulse output 37 onto a sample 65, which is mounted on a spinning wheel (having a rotational frequency of 133 Hz) to provide a fresh spot for ablation. The scattered LIBS signal is directly collected by placing a light collection fiber 67 next to the ablation spot (illustrated as side collection) and recorded by a compact spectrometer 69 such as one employing 178 nm-876 nm, which has Model No. USB4000 from Ocean Optics.

A LIBS spectra is directly recorded without using a gated-spectrometer. The atomic emission peaks are much brighter than the broad plasma continuum emission. The low continuum emission also indicates little thermal emission and helps limit the heat-affected zone in material processing and micromachining. The simple detection system requirements further reduce the complexity and cost of the LIBS system. The fast repetition rate at about 1-2 MHz also enhances the accumulation of LIBS signals.

To further evaluate this system, the dependence of the LIBS signal on pulse fluence is also considered. The laser intensity and the corresponding LIBS signal monitored simultaneously using two spectrometers 69. The LIBS signal is collected in a backward direction via a fiber 71 and lens 73, to fully eliminate the scattered excitation light by a dichroic mirror 77. The LIBS signal goes back through the objective and is reflected by dichroic mirror 77 (having a long pass >900 nm). After an additional filter 75, the LIBS signal is focused using lens 73 and collected by compact spectrometer 69.

The LIBS signal is accompanied by a spectrally broad continuous plasma emission. With nanosecond pulses, this continuum can be very strong and overwhelms the atomic emission lines. Since atomic emission lines decay more slowly than the continuum signal, nanosecond LIBS systems typically employ expensive time-gated detectors to isolate the atomic emissions. <100 femtosecond duration pulses have been shown to significantly reduce the strength of the continuum, making the atomic emissions easily identifiable, thereby eliminating the need for a gated detector, which can account for a large portion of the cost of the apparatus. To obtain completely continuum-free spectra, mathematical methods can be used.

Ablation should first occur once the pulse is of sufficient energy that the peak fluence rises above the threshold in a small region in the center of the beam. As the pulse energy further increases, both the amount of ablation and the area ablated increase. The LIBS signal intensity increases almost linearly with total pulse fluence once the pulse energy is high enough that the majority of the focal spot contributes to the ablation. It is also noted that the strength of the LIBS signal is linearly proportional to repetition rate. The present apparatus is advantageously useful for ultrafast ablation of materials for dental and eye surgery, cutting tissue of a patient in a surgical unit (including a doctor or robotic-held laser beam emitting tool), endoscopy, dicing of semiconductor chip, scribing glass and other micromachining activities. A very fast repetition rate (1 MHz), with a high energy per pulse (0.1-10 micro Joule) and ultrafast (sub-picosecond) pulses are best. Multiple such ultrafast pulses within one picosecond perform better than a single pulse.

A manually portable and compact unit for the present ultrafast laser apparatus 111 is illustrated in FIGS. 5 and 6, which includes a long-fiber oscillator 113. This oscillator 113 is very similar to that of the prior laboratory version, however, this is an all fiber construction without "free space" components for the oscillator. The present embodiment uses a pump diode laser 117, a fiber combiner 119, a gain fiber 121, passive single mode fibers 123 and 129, and an isolator 141, similar to that of the FIG. 2 embodiment. Also, a pair of fiber polarization controllers 181 and 183 are employed adjacent an output coupler 185 of oscillator 141. An emitted output pulse is sent from output coupler 185 to a micromachining unit, and endoscope fiber unit or a LIBS spectrometer unit 191 via a detachable output fiber 193. An exemplary micromachining unit is disclosed in U.S. Patent Publication No. 2009/0188901 entitled "Laser Material Processing System" which published to Dantus on Jul. 30, 2009, and is incorporated by reference herein. The flexible coiling of gain 121 and long passive fibers 123 (and optionally 129), with at least passive fiber 123 being about 100 m long, having a loop outside diameter of about 150 mm and a loop width of about 13 mm, allow oscillator 113, including pump laser 117, to completely fit within a portable housing 195. Housing 195 is preferably smaller than $\frac{1}{10}$ m$^3$ (for example, 30 cm×30 cm×30 cm at dimensions a, b and c), and more preferably has outer dimensions less than $\frac{1}{100}$ m$^3$ (for example, 10 cm×10 cm×10 cm); housing 195 may have a generally cubic or rectangular cuboid shape. This compactness is ideally suited for use on a spacecraft, wheeled robotic device, and for manual transport within a person's backpack or hand-held unit.

It is noteworthy that an amplifier is not required with the present ultrafast laser apparatus, although it can optionally be used for some specialized instances such as for pulse train amplification. Nevertheless, the Yb doped optical fiber preferably emits a laser output pulse having a duration less than 1 ns, an unamplified energy greater than 100 nJ and more preferably greater than 300 nJ without amplification or a Q-switch, and has an oscillator repetition rate less than 10 MHz. The present Yb fiber laser advantageously achieves improved quantum efficiency over conventional Er fiber lasers. For example, both Yb and Er gain fibers can be pumped by a 976 nm diode pump laser. The Er emission will be 1500 nm, but the Yb emission is 1030 nm which is beneficially much closer to the pump wavelength of 976 nm. Therefore, the Yb fiber of the present laser system is significantly more efficient which leads to a greater energy output for less cost and component complexity. This is well suited for an ultrafast laser system emitting laser beam pulses each having a duration <1 ns and often <1 ps.

Figure 7:
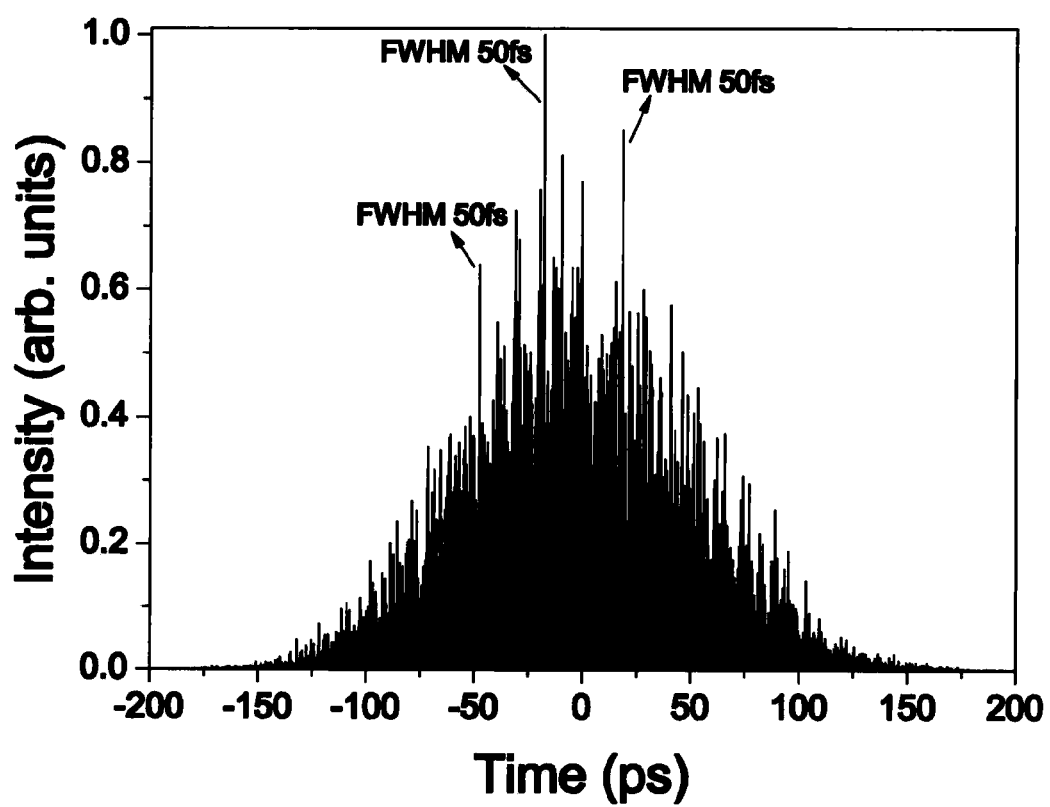
FIG. 7 is a graph showing a simulation of a temporal profile of output pulses with sub-pulse clusters.
Figure 8:
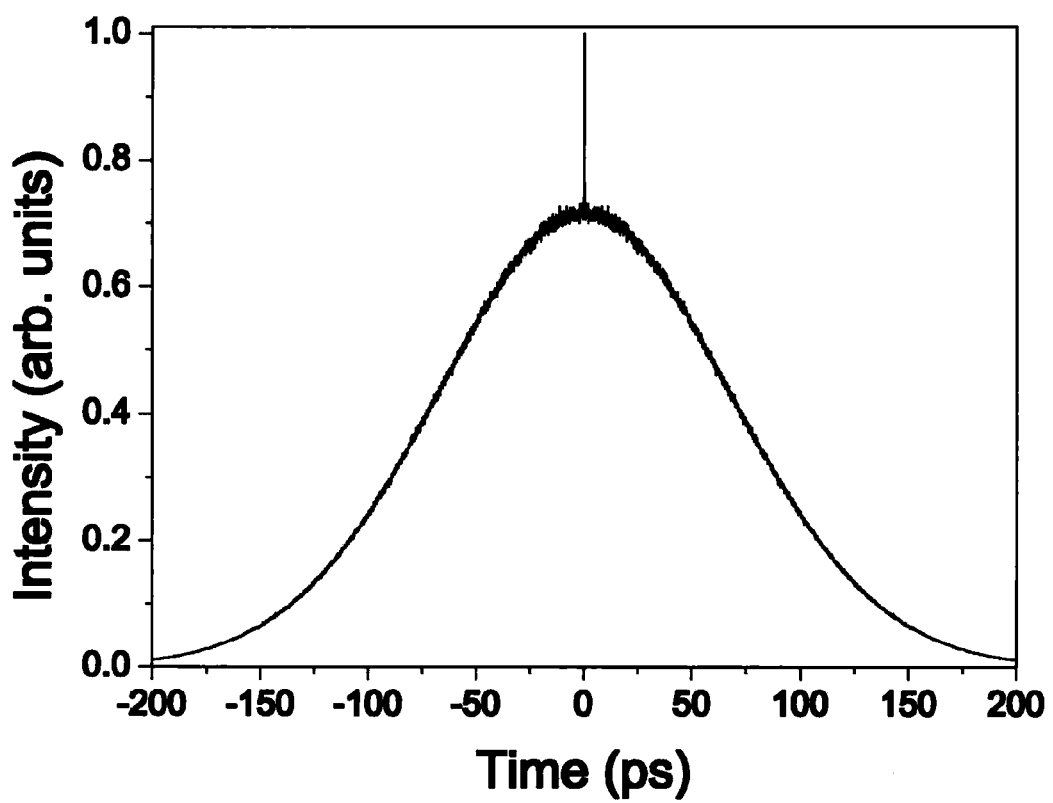
FIG. 8 is a simulation of an averaged autocorrelation of the output pulses with the sub-pulse clusters.

The present laser apparatus is ideally suited for producing trains or discrete sub-pulse clusters within a time period less than 200 femtoseconds, and more preferably less than 100 femtoseconds for material ablation, LIBS and selective Raman scattering. Neither active pulse shaping nor amplification is needed to obtain and use this train of sub-pulse clusters in the present apparatus, thereby significantly reducing component costs and complexity. Simulations of such sub-pulse clusters can be observed in FIGS. 7 and 8. Output pulse replication is performed with a Michelson interferometer, more preferably with birrefringent optics, or much more preferably with a gap in the gain fiber. At least two pulses are created from a single pulse, and because they have some phase distortion, the phase requirement for selective Raman excitation will be satisfied. Selective excitation requires minimum correlation functions that repeat every delta Raman shift. Delaying a pulse replica is equivalent to displacing its phase in the frequency domain. An external device can be used to create the pulse replica or it can be done intracavity through vibrational nodes selective excitation requiring a minimum correlation function:

$$P(\Delta) \propto |\int e^{i[\phi(\omega-\Delta)-\phi(\omega+\Delta)]} d\omega|^2 \qquad (5)$$

The pulse replica corresponds to a translated phase. Since the phase distortions are non-linear (e.g., quadratic, cubic, quartic), it ensures that greater selectively will be achieved.

While various aspects of the present invention have been disclosed, it should be appreciated that other variations are possible. For example, additional or fewer optical components, such as elimination of passive fiber 29, lenses, mirrors, and the like can be employed, although various advantages may not be achieved. Furthermore, a different pump laser can be used although the price and weight advantages of the present system may not be realized. Alternate doped fibers include Er-Yb mixed, Tm (thulium), and other dopants, although certain advantages may not be achieved. It is also envisioned that operation with different core fiber diameters from 2 microns to 200 microns may be provided. Alternately, the present system can reduce the repetition rate of an ultrafast fiber laser oscillator through the addition of a dispersive fiber instead of active pulse picking, to achieve repetition rates slower than 10 MHz, down to 1 MHz, and in some cases as low as 0.5 MHz. It should be also be appreciated that any of the features of the various constructions disclosed herein can be interchanged and replaced with any of the other constructions and embodiments, although certain advantages may not be realized. It is intended by the following claims to cover these and any other departures from the disclosed embodiments which fall within the true spirit of this invention.

The invention claimed is:

1. A laser apparatus comprising:
a fiber oscillator operably producing pulses with energy greater than 100 nJ and a pulse duration less than 200 fs; and
gain and passive fibers, at least one of the fibers having a length greater than 10 m, and the at least one fiber being flexibly looped with a loop diameter less than 150 mm without optical degradation.

2. The laser apparatus of claim 1, further comprising a laser pulse having a cluster of sub-pulses with duration less than 1 ps per sub-pulse and an unamplified energy greater than 100 nJ emitted from the oscillator fiber, and a duration of the cluster being greater than 100 fs.

3. The laser apparatus of claim 1, wherein the oscillator has a repetition rate less than 5 MHz and the emitted laser pulse has an unamplified energy greater than 300 nJ.

4. The laser apparatus of claim 1, wherein the emitted laser pulse creates discrete sub-pulses clustered together with a sub-pulse delay shorter than 3 ps, with each sub-pulse having a duration less than 1 ps, and the clustered sub-pulses are insensitive to dispersion, free of amplification.

5. The laser apparatus of claim 1, further comprising a portable housing, a diode pump laser and a spectrometer, the housing containing the entire oscillator and spectrometer, and the housing having an external size with a total volume less than 1/10 m3 excluding the diode pump laser in the volume.

6. The laser apparatus of claim 1, further comprising an endoscope fiber located downstream of the oscillator fiber.

7. The laser apparatus of claim 1, further comprising a specimen or workpiece, and a series of unamplified laser pulses emitted from the oscillator fiber and acting upon the specimen or workpiece.

8. The laser apparatus of claim 1, further comprising a Laser-Induced Breakdown Spectroscopy detection system including a spectrometer, located downstream of the fiber.

9. The laser apparatus of claim 1, further comprising a diode laser pumping the fiber oscillator.

10. The laser apparatus of claim 1, wherein the fiber oscillator comprises a Yb doped gain fiber.

11. The laser apparatus of claim 1, further comprising a micromachining unit receiving the pulses to ablate material.

12. The laser apparatus of claim 1, further comprising a surgical unit receiving the pulses to cut tissue.

13. The laser apparatus of claim 1, wherein the fiber oscillator exceeds a threshold of soliton stability and produces the pulses with energy of at least 300 nJ.

14. The laser apparatus of claim 1, wherein the fiber oscillator includes a fiber with a length of at least 100 m.

* * * * *